United States Patent [19]

Duncombe et al.

[11] 4,430,348

[45] Feb. 7, 1984

[54] IMMOBILIZED GLUCOAMYLASE REACTOR FOR PREPARING A LOW CALORIE BEER

[75] Inventors: George R. Duncombe, Grafton; William F. Line, West Allis; Etzer Chicoye, Wauwatosa, all of Wis.

[73] Assignee: Miller Brewing Company, Milwaukee, Wis.

[21] Appl. No.: 441,258

[22] Filed: Nov. 12, 1982

Related U.S. Application Data

[63] Continuation-in-part of Ser. No. 116,377, Jan. 29, 1980, abandoned, and Ser. No. 253,468, Apr. 13, 1981, abandoned.

[51] Int. Cl.$^3$ .................. C12C 11/04; C12N 11/14; C12M 1/40
[52] U.S. Cl. ............................ 426/13; 426/16; 435/176; 435/288
[58] Field of Search ................ 426/13, 16, 11; 435/174, 176, 179, 288

[56] References Cited

U.S. PATENT DOCUMENTS

| | | | |
|---|---|---|---|
| 3,379,534 | 4/1968 | Gablinger | 426/16 |
| 3,519,538 | 7/1970 | Messing et al. | 435/176 |
| 3,705,084 | 12/1972 | Reynolds | 435/180 |
| 3,970,521 | 7/1976 | Zaborsky et al. | 435/179 |
| 4,013,514 | 3/1977 | Wildi et al. | 435/179 X |
| 4,051,011 | 9/1977 | Miyauchi et al. | 435/288 X |

FOREIGN PATENT DOCUMENTS 1421955 1/1976 United Kingdom .

OTHER PUBLICATIONS

Vieth, et al., Design and Analysis of Immobilized Enzyme Flow Reactors, Applied Biochemistry and Bioengineering, vol. I, 1976, (pp. 221–234).
Wang, et al., Collagan-Enzyme Complex Membranes and Their Performance In Biocatalytic Modules, Biotechnol. & Bioeng., vol. XV, 1973, (pp. 93–115).
Zaborsky, O. R., Immobilized Enzymes-Miscellaneous Methods and General Classification Methods in Enzymology, vol. XLIV, 1976, (pp. 317–332).

*Primary Examiner*—David M. Naff
*Attorney, Agent, or Firm*—Quarles & Brady

[57] ABSTRACT

A superattenuated low caloric beer is produced by passing fermenting beer through an immobilized glucoamylase reactor having active glucoamylase immobilized on a ceramic monolith. The ceramic monolith has open ended passages ranging from 50 to 3,000 microns in diameter through which the beer passes, and glucoamylase is covalently bonded to internal surfaces of the passages. The glucoamylase is preferably covalently bonded by reacting an aldehydic derivative of glucoamylase with an aminofunctional group on the internal surfaces of the passages to form an aldimine which is reduced to a secondary amine. The reactor can sustain high flow rates of beer containing yeast and other particulate matter without plugging or fouling, and it is operationally stable under fermentation conditions over a long period of time.

5 Claims, 3 Drawing Figures

IMMOBILIZED GLUCOAMYLASE REACTOR FOR PREPARING A LOW CALORIE BEER

RELATED CASES

This application is a continuation-in-part of our earlier application Ser. Nos. 116,377 and 253,468 filed Jan. 29, 1980 and Apr. 13, 1981, respectively, both now bandoned.

FIELD OF THE INVENTION

The present invention relates to a novel immobilized glucoamylase reactor and a method of employing the reactor to superattenuate a lager beer during primary filtration.

BACKGROUND OF THE INVENTION

A typical lager sweet wort consists of a complex mixture of starch derived carbohydrates, which are classified as fermentable or non-fermentable according to whether they can be converted into ethanol by brewer's yeast. The fermentable carbohydrates are formed by hydrolysis of grain starches by two enzymes, $\alpha$ and $\beta$ amylase, derived from malted barley. In most American lagers malted barley also serves as the predominant starch source while a smaller proportion is derived from nondiastatic adjunct grains. In the United States, corn grits and #4 brewer's rice are the predominant adjuncts.

All grain starches are glucose homopolymers in which the glucose residues are linked by either $\alpha$-1,4 or $\alpha$-1,6 bonds. During the mashing cycle the starches are first solubilized and then a portion of the solubilized large starch molecules are hydrolyzed to three low molecular weight sugars which brewer's yeast can ferment to ethyl alcohol. The major fermentable sugars are glucose, maltose, and maltotriose while traces of sucrose and fructose are also present. The nonfermentable or limit dextrin fraction consists of all sugars of a higher degree of polymerization (DP) than maltotriose. The bulk of the limit dextrin fraction is composed of polysaccharides which are greater than 10,000 molecular weight.

As indicated above the hydrolysis of the grain starches is catalyzed by two amylases endogenous to malted barley. One, $\alpha$-amylase, is an endoamylase which randomly cleaves $\alpha$-1,4 bonds in the interior of the raw, largely insoluble starch molecules, fragmenting it into large but soluble polysaccharides termed dextrins. The second $\beta$ amylase is an exo-amylase which sequentially cleaves $\alpha$-1,4 bonds from the non-reducing end of these dextrins producing the three fermentable sugars described above. Both enzymes are inactive towards the $\alpha$-1,6 linkages (branch points) of the starches (i.e. they are unsable to debranch the strach molecule) and this results in the formation of the limit dextrins described above.

After completing the mash cycle, the spent grains are removed by passing the mash through a lauter tun to obtain the clarified lager sweet wort. The wort is then transferred to a brew kettle and boiled vigorously for 1-2 hours to inactivate the malt enzymes. It is then cooled, pitched with yeast, and fermented at temperatures ranged from 8°-16° C. to convert the three sugars described above to ethanol. The composition of the wort can vary depending on the starting materials, mash cycle, and other variables. The carbohydrate composition of a typical wort consists of 65-80% fermentable sugars, and limit dextrins ranging from 20-35%. At end of fermentation the fermentable fraction would be converted to ethanol at a final concentration ranging from 3-6% w/w. The limit dextrins are not converted during fermentation and form the bulk of the dissolved solids, commonly referred to as real extract, in the final beer.

Recently, reduced calorie beers have become popular in the U.S. beer market. These beers may be formulated by: (1) reducing both the alcohol and real extract concentrations in the beer to attain the desired calorie level, or (2) by hydrolyzing the limit dextrins with exogenous enzymes, one component of which is capable of debranching the limit dextrins. The latter method is advantageous since it allows one to attain the desired calorie level with a minimum reduction of the alcohol content of the packaged product. The enzyme most commonly used to hydrolyze the limit dextrins is glucoamylase, a nonspecific exoamylase derived from a variety of fungal sources (e.g. A. niger, R. delmar, etc.) [1]. The enzyme is active vs. both $\alpha$-1,4 and $\alpha$-1,6 linkages and therefore is capable of completely hydrolyzing starch to glucose. It attacks the starch molecule from the nonreducing end producing glucose as the sole end product. It is also active vs. starch derived oligosaccharides, e.g. maltose, maltotriose, isomaltose, etc.

In theory debranching enzymes may be added at any time during the brewing process. In practice brewers prefer to add them in fermentation because the fermentation process itself requires 6-15 days depending on pitching rate, fermentation, temperature, etc. In contrast the brewhouse operations are of much shorter duration (2-4 hrs/brew) and it operates under tight scheduling constraints. Therefore these enzymes are employed as fermentation adjuncts as taught by Gablinger in U.S. Pat. No. 3,379,534, and the limit dextrins are hydrolyzed to fermentable sugars, which the yeast convert to ethanol. Operationally these beers ferment to a lower specific gravity due to: (1) increased alcohol, and (2) decreased real extract, than would the same beer without exogenous enzymes. Such beers are referred to as superattenuated beers. [2].

The exogenous enzymes described above are dissolved in the wort or beer. It would be economically adventageous to have a method of enzymatically treating beer without dissolving the enzymes in the beer. One method is to immobilize the enzyme on a water insoluble solid support or carrier in such a manner that: (1) the immobilized enzyme can be readily recovered and reused and (2) the system is stable to repeated use for a prolonged period of time.

Enzymes have been immobilized by adsorption, entrapment, and covalent attachment to a wide series of supports. Briefly, adsorption relies on electrostatic or van der Waals type bonds for attachment of the enzyme to the solid support. Thus, many enzymes have been adsorbed on various ion exchange resins, clays, etc. The entrapment method entails polymer formation from a solution containing the enzyme. The enzyme is then physically entrapped in the interstices of the polymer matrix as it is formed and remains there due to the fact that the enzyme is too large to diffuse from the matrix back into solution. This technique is frequently used for conversion of low molecular weight substrates which can diffuse into the matrix and contact the enzyme. Obviously, it cannot be used for conversion of macromolecular substrates since the very matrix entrapping the enzyme would not permit entry of large substrates and would thus prevent enzyme-substrate contact.

The final method involves covalent attachment of the protein molecule to a polymer bearing a reactive functional group. The enzyme may be attached via one of its free functional group (i.e., groups not involved in the peptide linkage). These include: (1) the amino group of lysine; (2) the phenolic ring of tryosine; (3) the $\omega$ COOH group of aspartic or glutamic acids; and (4) the imidazole ring of histidine. Another potentially reactive group is the carbohydrate moiety of glycoproteins. Theoretically covalent attachment should provide the most stable immobilized adducts.

The main reasons for immobilizing enzymes on water insoluble supports are: (1) recovery and reuse of the enzyme, (2) preparation of a relatively enzyme-free product, (3) to fashion the immobilized derivative into a reactor through which the substrate stream may be rapidly circulated and still effect conversion to the desired product and most importantly (4) to fashion an operationally stable system; i.e. one in which the immobilized derivative maintains its catalytic potency under the defined operating conditions for a large number of cycles over a long period of time.

Several types of immobilized enzyme reactors have been described in the literature [3]. The most prevalent are those in which the enzymes have been immobilized on particulate carriers. These include: (1) batch stir in which the immobilized adduct is stirred in the substrate stream and recovered by filtration, (2) plug flow or fixed bed in which the immobilized derivative is packed into a column and the substrate stream is passed through it in a manner similar to a column chromatography operation, and (3) fluidized bed, which is similar to plug flow except that the substrate stream is circulated into the bottom of the column at sufficiently greater flow rates to float or fluidize the bed.

Reactors have also been constructed from enzymes which have been immobilized on various membranes. Thus several enyzmes have been immobilized on collagen films, which were then fashioned into concentric cylindrical reactors [4, 6].

The reactor types fashioned from enzymes immobilized on particulate carriers are not suitable for processing a beer during primary fermentation. First of all, a fermenting beer stream (like many other industrial substrate streams) contains a large concentration of suspended solids formed or introduced as follows. When the wort is cooled after kettle boil, a heavy precipitate forms which is allowed to settle out in a tank. The precipitate (a mixture of protein, carbohydrate, etc.) is referred to as trub and the settling process is referred to as hot-break. Trub separation is not complete during the hot-break, and its formation continues even during fermentation. In addition, beer is pitched with a large (on the order of $1\times 10^7$ cells/ml of wort) concentration of brewer's yeast at the beginning of the fermentation. The yeast typically multiplies to six to nine times its original concentration at high kraeusen and then settles out as the specific gravity decreases toward the end of fermentation.

In addition to trub formation and yeast multiplication there are two other major changes that occur during fermentation: (1) large quantities of $CO_2$ are evolved during active fermentation, and (2) the specific gravity of the beer decreases markedly throughout.

Finally, it is economically necessary for brewers to reclaim most of the expanded yeast crop at end fermentation to repitch fresh wort in order to supplement the crop produced by primary propagation. Typically brewers are able to pitch 3-6 fresh fermentations with the yeast reclaimed from one fermenter.

With these facts in mind, it becomes clear why the three particulate reactors described above are not suited to this stream:

(1) The batch stir system is impractical since it would require that the yeast and the immobilized derivative be separated from each other at end of fermentation in order to recover and reuse both the enzyme conjugate and the yeast cream. This separation would prove both difficult and costly.

(2) The plug flow reactor could not support flow of a substrate stream containing large and variable levels of suspended solids typical of a fermenting lager stream. Such a system would rapidly plug as the solids (yeast and trub) accumulated on top of the immobilized enzyme bed.

(3) Fluidized beds are impractical since the density of the fermenting beer stream is continuously decreasing during fermentation. Since particle flotation is dependent on the density of the supporting medium, the flow rate would have to be continuously increased throughout fermentation to compensate for the density decrease in order to keep the bed fluidized. In addition, during active fermentation the large quantities of $CO_2$ evolved would disrupt the even flow of liquid and make fluidization more difficult and possibly channel the bed. Most fluidized bed reactors contain support retainers at both ends in order to prevent flow of the adduct back into the substrate feed tank or into the product receiver. The suspended solids could accumulate at the retainers and block flow. Finally at end of fermentation the adduct would have to be separated from the yeast that would be entrained with the residual beer.

Membrane reactors of the type described in the literature [4, 5] suffer from the fact that the membranes lack strength and require backing on large amounts of inert support materials.

Immobilized glucoamylase reactors have been applied to the production of high glucose syrups from liquefied corn starch. These substrates are readily soluble in water at concentrations up to 40% w/w and present none of the problems attendant to a fermenting beer stream as described above. Thus most conventional plug flow reactors are able to handle these substrate streams. British Pat. No. 1,421,955 by Woodward and Bennett discloses the use of a glucoamylase immobilized on a particulate carrier to: (1) sweeten an ale or stout post fermentation by contacting the end fermented beverage with immobilized glucoamylase (GA) in order to hydrolyze the limit dextrins to glucose, and (2) to convert clarified sweet wort limit dextrins to glucose prior to fermentation. They also state that a fluidized bed reactor fashioned from this carrier could work during fermentation, but the patent describes no such use of a fluidized bed reactor. Further such a reactor is impractical in a production situation for the reasons discussed above, i.e. rapidly changing fluid density, plugging at retainers, $CO_2$ evolution, and necessity of separating the conjugate from the yeast.

Most commercial glucoamylase is isolated from the mold *Aspergillus niger*. The glucoamylase produced by this microorganism is extracellular. The enzyme is a glycoprotein containing approximately 16% carbohydrate [7]. It is known that the hexose residues of the sugar moiety of glycoproteins may be oxidized by periodic acid to yield a protein containing reactive aldehydic functional groups. The resulting aldehydes may then be reacted with supports possessing primary amines in aqueous media under mild conditions to form the aldiminine or Schiff's base derivatives (Zaborsky U.S. Pat. No. 3,970,521).

SUMMARY OF INVENTION

It is the primary object of the present invention to describe the superattenuation of beer during fermentation utilizing a novel reactor in which glucoamylase is covalently attached to a non-particulate, rigid, incompressible inorganic carrier which has been rendered aminofunctional.

The reactor of the present invention (1) is capable of sustaining a rapid flow of a fermenting beer stream containing large quantities of suspended solids without plugging or fouling, (2) can operate at predetermined flow rates which are unaffected by density changes and $CO_2$ evolution, (3) is operationally stable under fermentation conditions, (4) allows yeast reclamation from the end fermented beer with no special processing, (5) can be readily cleaned in place, and (6) can therefore substitute for the soluble enzyme with minimum modification of the standard brewery production protocol as outlined above.

The novel reactor of the present invention consists of a ceramic monolith having a number of discrete openings or cells within an external core. For a monolith of given cross-sectional area, the number of internal cells (and therefore the individual cell size) may vary. For enzyme immobilization the maximum surface area (large number of small cells per unit cross section) is desired so that the maximum amount of enzyme can be attached and the reactor size can be minimized. At the same time the internal cell size must be sufficiently large to permit unobstructed passage of the suspended solids (particularly yeast) contained in the fermenting beer at high rates of flow.

The internal cell size of the monolith reactor of the present invention should be at least 50 micron to permit the unobstructed flow of the yeast and other undissolved solids present in the fermenting stream. At the same time they should be no greater than 3000 micron in order to present the maximum surface area for enzyme coupling. In the practice of this invention the preferred cell sizes ranged from 900–3000 micron [a core containing 600–100 cells/in$^2$]. The internal cells may be fashioned into several geometric configurations, such as square, triangle, hexagonal, and circular, while the shape of the external core can be similarly varied and is generally shaped to fit the reactor container.

It is another object of the invention to disclose a method of covalently attaching glucoamylase derivative to the ceramic monolith to form an immobilized enzyme carrier combination which is stable under the acidic conditions of a fermenting beer stream. In the present invention, a fully active glucoamylase whose carbohydrate moiety has been oxidized with periodic acid is covalently attached to a ceramic monolith which has been treated to render it aminofunctional. In an improvement on the prior art method the Schiff's base that forms is then reduced to form the more stable secondary amine.

It is the further object of the invention to disclose the use of a reactor formulated with the ceramic monolith-glucoamylase conjugate in the preparation of a superattenuated low calorie beer during primary fermentation. The resulting reactor can sustain high flow rates of the complex stream described above without plugging or fouling; and it is operationally stable under fermentation conditions over a long period of time.

DESCRIPTION OF PREFERRED EMBODIMENTS

Figure 1:
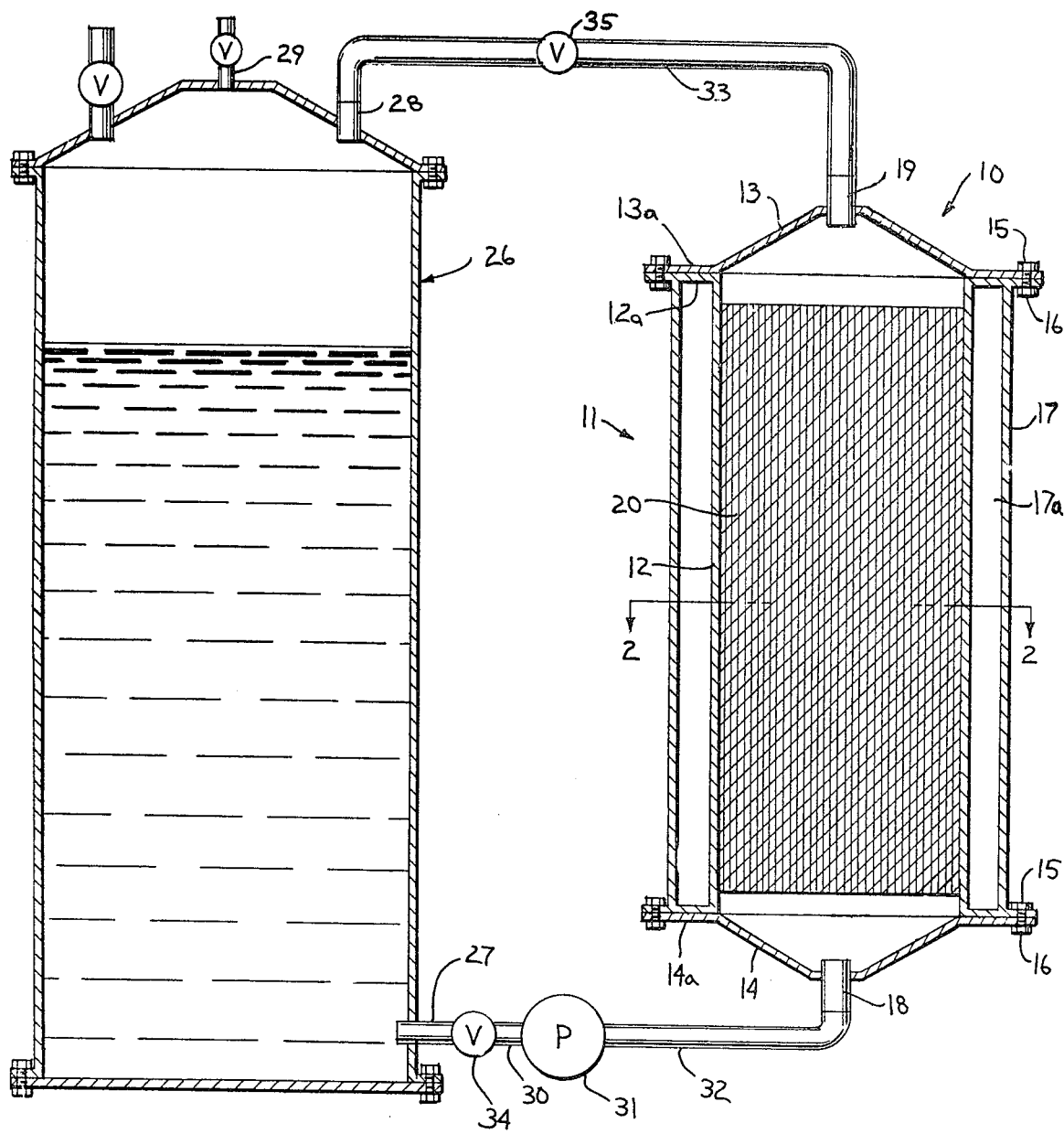
FIG. 1 is an elevational view, partly in section, showing a brewing fermentation tank and an enzyme reactor for use in practicing the method of the present invention.

In the preferred practice of the present invention, glucoamylase is immobilized on a ceramic monolith by covalently attaching an aldehydic glucoamylase derivative to an aminofunctional ceramic monolith.

The preferred method of immobilizing the glucoamylase on the ceramic monolith comprises: (1) oxidizing the carbohydrate moiety of glucoamylase to yield a derivative containing reactive aldehydic groups, (2) covalently attaching the resulting aldehydic glucoamylase (AGA) to an aminofunctional ceramic monolith of the type described above to form a Schiff's base, and (3) reducing the unstable Schiff's base to a stable secondary amine by reduction with $NaBH_4$.

The aldehydic glucoamylase is preferably oxidized by reacting the glucoamylase dissolved in an aqueous buffer between pH 4.5 and 6.0 with periodic acid. The addition rate of periodic acid is between 10 and 250-fold molar excess over glucoamylase (assumed M.W. 58,200). The reaction is run at room temperature for between 0.5 and 4 hours. Ethylene glycol (a 10-fold molar excess over periodic acid) is added prior to diafiltration of the AGA to consume any unreacted periodic acid.

In the preferred method of immobilization the enzyme is covalently attached to the monolith by contacting the monolith with a buffered, aqueous solution ranging in pH from about 5 to about 8.5 (e.g. 0.02 M $KHPO_4$ pH 8.0) to which the same buffer containing the AGA protein is added. The contact is allowed to continue at room temperature between 1 and 18 hours. The resulting AGA conjugate is then contacted with pH 8 buffer containing a reducing agent (e.g. $NaBH_4$) at about 4° C. for about 0.5 hours. The conjugate is then washed rigorously.

The chemical reactions which are involved may be illustrated as follows:

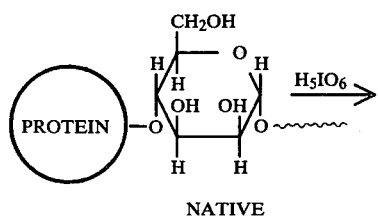

NATIVE

-continued

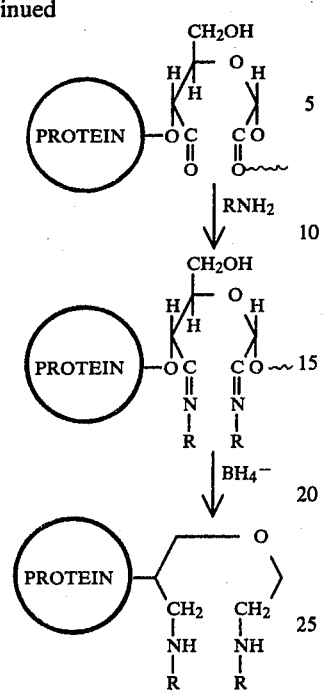

Wherein R is the water insoluble support or carrier.

In the drawings is shown one type of brewing apparatus in which the immobilized enzyme on the carrier can be used to make a superattenuated beer. As seen in the drawings the apparatus includes an enzyme reactor 10 comprising a tank 11 having a cylindrical main body section 12, a top cap 13 and a bottom cap 14. The caps 13 and 14 are fastened to the main body section 12 by the use of bolts 15 which extend through the aligned openings and nuts 16 which engage the bolts 15. This method of construction for the tank 11 is preferred as it permits the tank 11 to be disassembled and reassembled, when desired. Surrounding the main body section 12 is a cooling jacket 17 which provides a closed chamber 17a for receiving coolant to control the temperature of the contents of the tank 11. Although a cooling jacket of the type shown is preferred other means may be used to control the temperature of the contents of the tank.

Figure 2:
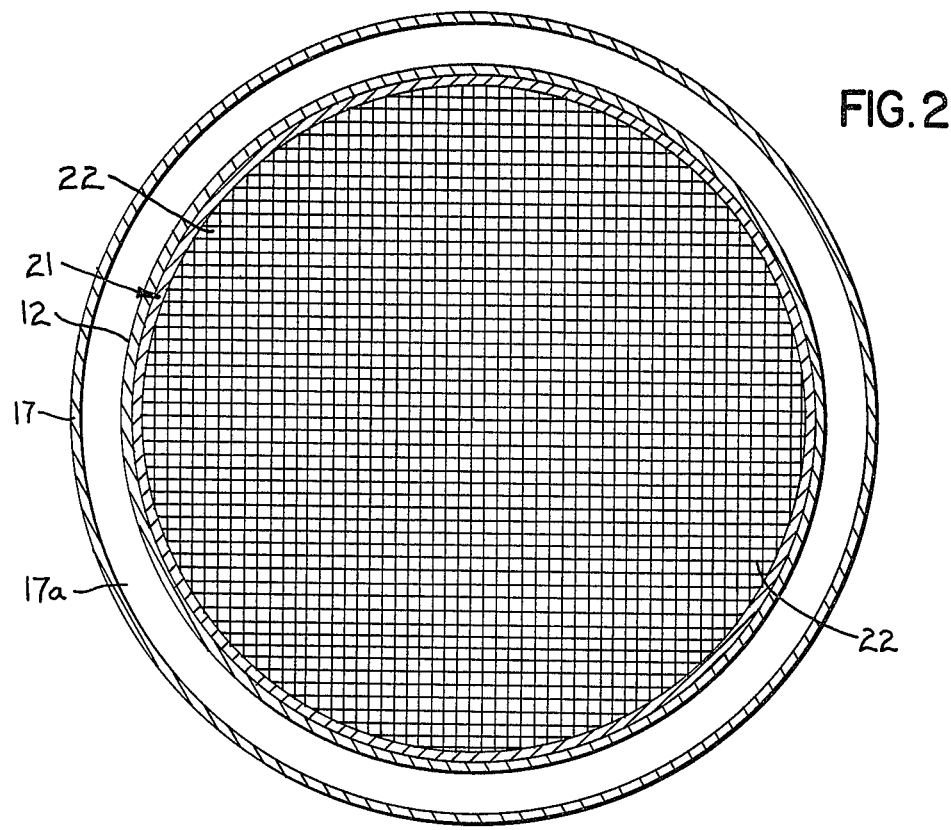
FIG. 2 is a sectional view taken along the lines 2—2 showing one form of a solid phase carrier.

As seen in FIG. 1, the tank 11 has an inlet 18 at the bottom and an outlet 19 at the top. Positioned in the tank 11 between the inlet 18 and the outlet 19 is a solid phase carrier 20 to which an enzyme (not visible) is attached. One form that the solid phase carrier 20 can take is shown in FIG. 2. As seen therein, the solid phase carrier comprises a circular ceramic body 21 which is sized to fit transversely across the main body section 12 of the tank 11. The ceramic body 21 has extending therethrough multiple flow passages 22. The flow passages 22 permit a brewing liquid containing suspended solids, such as yeast cells, to pass through the ceramic body 21 without the cells being filtered out or the passages 22 becoming clogged.

Referring once again to FIG. 1, it can be seen that the enzyme reactor 10 is positioned adjacent to and is connected to a fermentation tank 26. Although the fermentation tank 26 is shown as a cylindrical tank, it will be appreciated that it can take any conventional form. The fermentation tank 26 has an outlet 27 and an inlet 28 for connecting the tank 26 to the enzyme reactor 10. The outlet 27 is preferably located at the bottom of the fermentation tank 26 and the inlet 28 is preferably located at the top of the tank above the normal liquid level in the tank. The normal liquid level is shown in FIG. 1. In addition to the inlet 28 and the outlet 27, the fermentation tank 26 may be provided with other openings or ports such as the carbon dioxide vent 29 which can be seen in FIG. 1.

Still referring to FIG. 1, it can be seen that the interior of the fermentation tank 26 is connected to the enzyme reactor 10 by a first length of tubing 30 which connects the outlet 27 to the inlet of a pump 31. A second length of tubing 32 connects the outlet of the pump 31 to the inlet 18 of the enzyme reactor 10. The pump 31 may be of any type which is capable of forcibly propelling a brewing liquid which contains suspended solids without clogging the pump mechanism. A third length of tubing 33 connects the outlet of the enzyme reactor to the inlet 28 of the fermentation tank 26. When the fermentation tank 26 and the enzyme reactor 10 are joined together with the three lengths of tubing 30, 32 and 33, a closed system is formed. Flow through the system is controlled by valves 34 and 35 and the pump 31.

In use, the fermenting beer, which contains suspended yeast cells, is pumped from the fermentation tank 26 to the enzyme reactor 10 and back to the fermentation tank 26. The brewing liquid as it is propelled through the flow passages 22 or 25 in the solid phase carrier 20 or 23 comes into contact with the immobilized enzyme. The pumping of the brewing liquid through the closed system to achieve repeated contact with the immobilized enzyme continues until experience or testing indicates that the desired effect of the enzyme on the brewing liquid has been obtained. As the brewing liquid is being pumped through the closed system, the valves 34 and 35 are, of course, open. When it is desired to isolate the fermentation tank 26 from the enzyme reactor 10, the valves 34 and 35 are closed.

In the Examples, the following analytical procedures were used.

Protein was determined by a modified Lowry method [8]. Glucoamylase activity was determined vs. 1% soluble starch in 0.2 M acetate buffer at pH 5.0 and 37° C. The appearance of glucose was monitored with a Yellow Springs Model 27 Industrial Analyzer. One unit of activity was defined as the production of one micromole glucose per minute under these conditions.

Aldehydic groups in the protein was quantitated using 3-methyl-2-benzothiazolone hydrazone with propionaldehyde as the standard. The procedure was used to determine the increase in aldehydic functionality of glucoamylase after treatment with periodic acid [9].

The fermentations were monitored by the decrease in specific gravity using the Mettler/Paar DMS-45 calculating densitometer. When the beers were judged to be end-fermented, refractive indices were obtained on a Zeiss immersion refractometer. These measurements were used to calculate the alcohol and real extract [9–11] of the beers. The caloric content of a standard 12 oz. container was calculated at 3.3 g/100 ethanol [12].

Carbohydrate profiles were obtained by high pressure liquid chromatography on Bio-Rad Q15S resin. Diafiltrations were performed on an Amicon DC-2 apparatus equipped with an H-1P-10 cartridge (M.W. cutoff-10,000).

The quantity of active enzyme released from the supports into the beers was measured by incubating 1 ml of end-fermented beer with 4 ml, 2% w/v soluble starch dissolved in 0.2 M acetate buffer pH 5.0 at 50° C. The glucose released was monitored using the YSI Model 27 Industrial Analyzer. One leakage unit activity (L.U.) was defined as the production of one micromole glucose per hour under these conditions.

In all the fermentations in the Examples, the wort used was mashed as an all-malt wort and was adjusted to 12°–15° P with a commercial corn-derived syrup, prior to fermentation. In the Examples, the original gravity was constant. The worts were pitched with a stock brewing culture of *S. uvarum* to a final concentration of $1 \times 10^7$ cells/ml after the wort had been vigorously aerated. Fermentations were carried out at 15° C. in a constant-temperature room.

EXAMPLE 1

Aldehydic glucoamylase (AGA) was prepared from glucoamylase (Novo 150, Novo Laboratories, Inc., Wilton, CT). Initially, the enzyme was diafiltered versus water until the permeate was free of 280 nm absorbing material. The retentate was freeze dried and stored at 4° C. until used.

To a stirred solution of glucoamylase (360 mg protein in 200 ml of 0.05 M acetate buffer, pH 5.6) in a vessel shielded from light was added 4 ml of a 2.2% w/v periodic acid solution. The mixture was stirred at 25° C. for 4 hours, after which 0.25 ml of ethylene glycol was added and the mixture stirred for 30 minutes. Ethylene glycol was added to consume the unreacted periodic acid. The AGA preparation was then diafiltered vs. 10 volumes of $H_2O$ and used in the coupling reaction within one day.

The AGA preparation described above contained 144 nanomoles aldehyde equivalents per milligram protein as opposed to the native enzyme which contained only 3 nanomoles aldehyde equivalents per milligram protein. The AGA preparation was virtually as potent (22.8 u/mg protein) as the native glucoamylase (23.1 u/mg protein).

EXAMPLE 2

A ceramic monolith of the type illustrated in FIG. 2, containing internal cells 1500 microns in diameter and 200 cells per square inch, was coated with colloidal silica to increase the active surface and then reacted with 3-triethyoxysilylaminopropane to introduce the aminofunctional group. This organofunctional monolith was supplied by Corning Glass Works, Corning, NY. An AGA monolith reactor was prepared by placing 11 pieces (approximately 4.5" diameter by 3" thick) of the aminofunctional ceramic monolith in a jacketed Fischer-Porter glass chromatographic column (5×50 cm). The monolith was washed by pumping: (1) 10 liters water, and (2) 4 liters 0.02 M phosphate buffer pH 8.0 through the column. The column was drained, and 1 liter of 0.02 M phosphate buffer, pH 8.0 containing AGA, prepared as in Example 1 at a concentration of 4 mg protein/ml, was recirculated through the column by pumping up from the bottom. The enzyme solution was recirculated for 18 hours at a flow rate of 100 milliliters per hour. The column was then drained and cooled to 8° C. Two liters of 0.02 M $K_2HPO_4$, pH 8.0 containing 0.02 M $NaBH_4$ were pumped through the column in 30 minutes.

The column was washed by pumping the following solutions through the column: (1) 0.1 M phosphate buffer-1 M NaCl, pH 8.0, (2) water, (3) 0.1 M phosphate buffer, 1 M NaCl, pH 3.5, and (4) water. Finally the reactor received a wash with 1% w/v maltose at pH 5.0. Maltose is a substrate for glucoamylase and would be expected to remove any strongly non-covalently linked asorbed enzyme. The column was flushed with water, drained, and stored in 0.1% w/v sodium benzoate prior to use and between cycles. The monolith coated with colloidal silica prior to silylation will be referred to as reactor I.

EXAMPLE 3

A second reactor was constructed from a ceramic monolith of similar dimensions, but whose melt composition was different from the monolith of Example 2. The surface area of this monolith was high enough that it was silylated with 3-triethoxysilylaminopropane directly without the colloidal silica coating. A reactor was prepared from this material and AGA was covalently attached to it in the same manner as described in Example 2 for reactor I. This reactor will be referred to as reactor II.

EXAMPLE 4

Fermentations were conducted to compare the aldehydic glucoamylase with the native glucoamylase. The previously described wort was fermented with: (1) no enzyme added (Beer #1) to establish the attenuation limit; (2) with the native glucoamylase (Beer #2); and (3) with the AGA of Example 1 (Beer #3). The latter two fermentations were run to establish the superattenuation limits using both native glucoamylase (Beer #2) and aldehydic glucoamylase preparations (Beer #3). In both cases, the enzymes were added to the worts at the same final concentration at the start of fermentation.

Table 1 lists the properties of the end-fermented beers described above. The enzyme-free control (Beer #1) contained 0.5–0.6 g/100 less alcohol at end-fermentation than did either Beers #2 or #3. When packaged at 3.3 g/100 ethanol, Beers #2 and #3 contained about 1 g/100 less real extract than did Beer #1. At this alcohol concentration, Beers #2 and #3 would contain 92–93 cal/12 oz. as opposed to 108 cal/12 oz for the no-enzyme control.

Both native and AGA preparations survived fermentation as shown in Table 1. Thus, both Beers #2 and #3 contain 24–25 LU/ml when the beers were assayed as described above.

The carbohydrate composition of the beers at end-fermentation is listed in Table 2. Beers #2 and #3 have nearly identical compositions and differ from Beer #1 in that the nonfermentable sugars (>DP-3) have been reduced by 1.8–1.9 g/100.

The data indicated that there was substantially no difference between the beers produced with either native or aldehydic glucoamylase.

EXAMPLE 5

Preparation of a superattenuated low calorie beer using the AGA-ceramic monolith reactors Superattenuated beers (Beers 4 and 5) were successfully produced using the aldehydic glucoamylase-ceramic monolith reactors of Examples 2 and 3, as a substitute for soluble glucoamylase. The enzyme reactors were connected to a fermentation tank as shown in FIG. 1 and were used to routinely process 30 liters fermenting beer at 15° C. The beers were circulated in a closed loop from the bottom of the fermentation tank, through the enzyme reactor, from the bottom to the top, and back into the top of the fermentation tank, at a flow rate of about 1.3 liter/hour.

Beers 4 and 5 (Tables 1 and 2) are typical of the beers produced using the enzyme reactors. Beers 4 and 5 were similar to Beer #2 in specific gravity and carbohydrate composition at end-fermentation. When packaged at 3.3 g/100 ethanol, beers 4 and 5 also were nearly identical to Beer #2 in real extract and caloric content. Analysis of the end-fermented beers revealed that they contained 3–4% as much enzyme as Beer #2, indicating stable covalent bond formation between the AGA and the monoliths.

EXAMPLE 6

Demonstration of Operation Stability of the AGA-Ceramic Monolith Reactor

Figure 3:
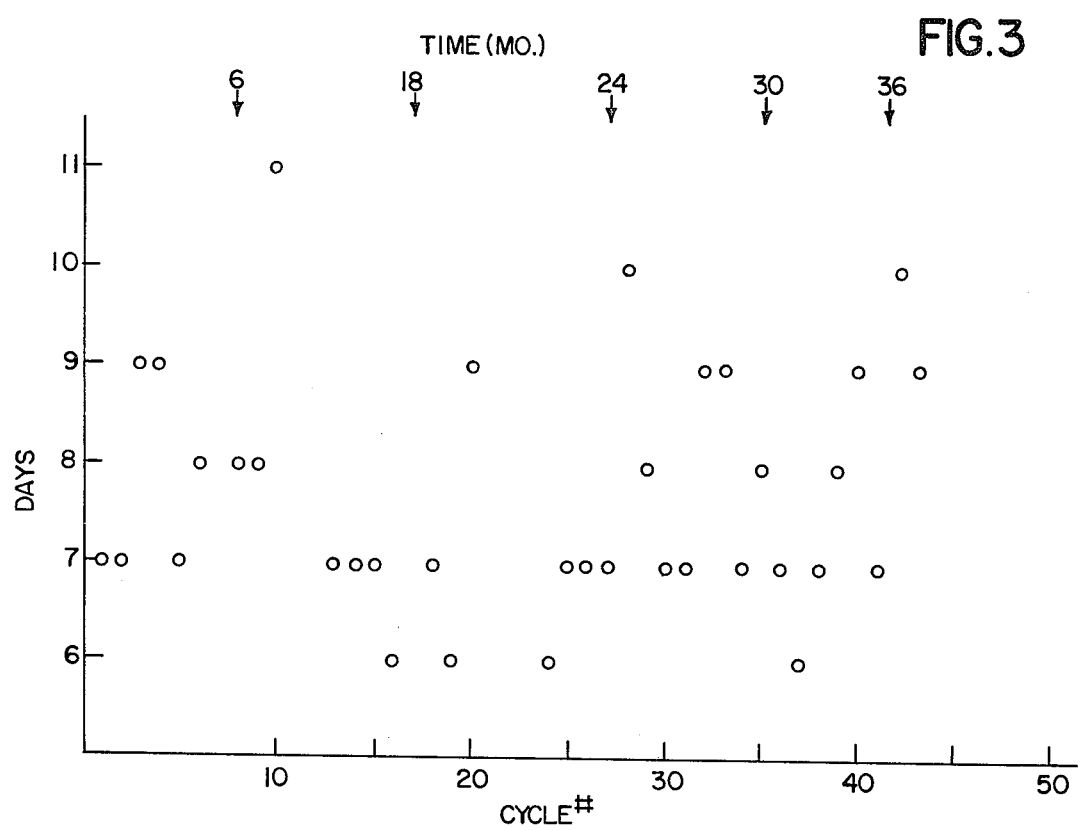
FIG. 3 is a graphic representation of data obtained in the preparation of a low calorie beer using the reactor of the present invention.

Several fermentation cycles were performed as described in Example 4 in order to test the operational stability of the two reactors. In between cycles, the reactors were flushed rapidly with water to remove any retained beer, yeast, etc. and stored under 0.1% w/v sodium benzoate when not in use. The data for reactor I is depicted in FIG. 3. To date this reactor has completed 44 thirty liter cycles over a period of 3 years with no systematic increase in fermentation time. As shown in FIG. 3, the time required to superattenuate the beer to the desired level varied randomly between 6–9 days. Reactor II, which was constructed after reactor I, has completed 19 thirty liter cycles with no systematic increase in the time required to superattenuate the beer to the desired level. Its performance appears to be identical to reactor I.

Reactor II was also used to treat fermentations of 60 and 72 liters. The purpose of these fermentations was to determine the maximum amount of fermenting wort that could be successfully treated by the reactor within the normal time span for a typical fermentation with soluble enzyme (i.e. 12 days or less). Reactor II was able to successfully treat 72 liters of fermenting wort within the allowable time span.

TABLE 1

ALCOHOL, REAL EXTRACT, AND CALORIE CONTENT OF SUPERATTENUATED BEERS AT END-FERMENTATION

| Beer # | Enzyme Source | Days Fermented | Specific Gravity at End-Fermentation | Real Extract at 3.3% Alcohol | Cal/12 oz. | Enzyme in Beer at End-Fermentation LU/ml | % Beer #2 |
|---|---|---|---|---|---|---|---|
| 1 | enzyme-free control | 13 | 1.0029 | 1.99 | 108.3 | 0 | 0 |
| 2 | soluble glucoamylase | 12 | 0.9965 | 0.99 | 92.5 | 25 | 100 |
| 3 | soluble AGA | 13 | 0.9966 | 1.01 | 92.4 | 24 | 96 |
| 4 | Reactor I | 7 | 0.9963 | 0.97 | 92.2 | 0.92 | 3.7 |
| 5 | Reactor II | 7 | 0.9960 | 0.94 | 91.8 | 0.76 | 3.0 |

TABLE 2

CARBOHYDRATE PROFILES OF BEERS AT THE END OF FERMENTATION

| Beer # | Enzyme Source | Carbohydrate (g/100 ml) | | | | |
|---|---|---|---|---|---|---|
| | | Total | DP-1* | DP-2* | DP-3* | >DP-3* |
| 1 | enzyme-free control | 2.40 | 0.01 | 0.13 | trace | 2.26 |
| 2 | soluble glucoamylase | 0.85 | 0.08 | 0.21 | 0.17 | 0.39 |
| 3 | soluble AGA | 0.76 | 0.04 | 0.18 | 0.20 | 0.34 |
| 4 | Reactor I | 0.69 | 0.05 | 0.12 | 0.16 | 0.36 |
| 5 | Reactor II | 0.74 | 0.03 | 0.17 | 0.18 | 0.36 |

DP = Degree of polymerization; DP-1 assumed to be glucose, DP-2 assumed to be maltose, DP-3 assumed to be maltotriose.

While a preferred embodiment has been described, it will be readily apparent to those skilled in the art that a number of modifications and changes may be made without departing from the spirit and scope of the invention. Therefore, it is intended that the scope of the invention should not be limited by the description of the preferred embodiment, but only by the claims which follow.

REFERENCES

1. Pazur, J. *Methods in Enzymology*, XVIII, (ed. Ginsberg, V.), Academic Press (1975), p. 931.
2. Andrews, J. et al. *J. Inst. Brew.*, 58 (1952), p. 189.
3. Lilly, M. D. and Dunhill, P. *Methods in Enzymology*, XLIV (1976), p. 717.
4. Wang, S. and Vieth, W. *Biotech. Bioeng.* XV, (1973), p. 93.
5. Vieth, W. and Venkatasubramanian, K. *Methods in Enzymology*, XLIV, (1976), p. 243.
6. Lin, P. et al. *J. Food Sci.*, 41 (1976), p. 1056.
7. Pazur, J. et al. *ABB III* (1965), p. 351.
8. Miller, G. *Anal. Chem.*, 31 (1959), p. 964.
9. Kneen, E. (ed.). "Alcohol Determined Refractometrically," in *Methods of Analysis of the American Society of Brewing Chemists*, 7th revised edition, published by the Society (1976).
10. Olhansen, J. *Brewers Digest*, 27, (1952), p. 45.
11. Olhansen, J. *Brewers Digest*, 27, (1952), p. 53.
12. Helbert, J. *J. Amer. Soc. Brew. Chem.* 36 (1978), p. 66.
13. Marinelli, L. (Chairman). *JASBC*, 35 (1978), p. 104.
14. Scobell, H., et al. *Cereal Chem*, 54 (1975), p. 905.

We claim:

1. In the method of preparing a superattenuated low calorie beer by hydrolyzing the limit dextrins in beer with glucoamylase, the improvement which comprises passing the beer containing the limit dextrins during primary fermentation through a ceramic monolith having a plurality of open ended passages ranging from 50 to 3,000 microns in diameter extending therethrough to permit the rapid, sustained, unobstructed flow of a fermenting beer stream containing yeast and other suspended solids, said passages having surfaces to which glucoamylase has been covalently attached to form an immobilized glucoamylase reactor, which reactor effectively hydrolyzes the limit dextrins in the beer with which it comes in contact without releasing the attached enzyme.

2. The method of claim 1 in which the glucoamylase has been covalently attached by oxidizing the carbohydrate moiety of glucoamylase to obtain an aldehydic derivative and coupling said derivative to the monolith bearing aminofunctional groups and then reducing the resulting aldimine to form a secondary amine.

3. In the method of preparing a reduced calorie beer by hydrolyzing the limit dextrins in the beer with glucoamylase, the improvement which comprises passing a beer containing limit dextrins together with yeast and other particulate matter from a fermenter through an enzyme reactor containing a ceramic monolith having a plurality of passages extending therethrough which range from 50 to 3,000 microns in diameter and which permit the beer and its contents to pass therethrough without fouling or plugging, said passages having surfaces thereof containing covalently bonded glucoamylase obtained by reacting an aldehydic derivative of glucoamylase with an aminofunctional group on said surfaces to form an aldimine which is reduced to a secondary amine.

4. An immobilized enzyme reactor useful for preparing a superattenuated low calorie beer, said reactor comprising a ceramic monolith having a plurality of open ended passages ranging from 50 to 3,000 microns in diameter, each passage having surfaces containing glucoamylase covalently attached thereto, the passages permitting the rapid, unobstructed, sustained flow of a fermenting beer stream containing yeast and other suspended solids therethrough for the duration necessary to convert a brewer's wort containing limit dextrins to a superattenuated low calorie beer during primary fermentation by said covalently attached glucoamylase hydrolyzing the limit dextrins to form glucose which is converted to alcohol by the yeast.

5. The reactor of claim 4 in which an aldehydic glucoamylase is covalently attached to a monolith containing amino functional groups and the resulting aldimine is reduced to a secondary amine.

* * * * *